L. C. LAWRENCE.

ARTIFICIAL LIMB.

APPLICATION FILED AUG. 20, 1919.

Reissued Dec. 14, 1920.

15,006.

3 SHEETS—SHEET 1.

Inventor

Louis C. Lawrence,

By Howson and Howson

Attorney

L. C. LAWRENCE.

ARTIFICIAL LIMB.

APPLICATION FILED AUG. 20, 1919.

Reissued Dec. 14, 1920.

15,006.

3 SHEETS—SHEET 2.

Inventor

*Louis C. Lawrence,*

By Howson and Howson

Attorney

L. C. LAWRENCE.

ARTIFICIAL LIMB.

APPLICATION FILED AUG. 20, 1919.

Reissued Dec. 14, 1920. 15,006.

3 SHEETS—SHEET 3.

Inventor

*Louis C. Lawrence,*

By *Howson and Howson*

Attorney

UNITED STATES PATENT OFFICE.

LOUIS C. LAWRENCE, OF BROOKLYN, NEW YORK, ASSIGNOR, BY DIRECT AND MESNE ASSIGNMENTS, TO LAWRENCE ARTIFICIAL LIMB CO., INC., A CORPORATION OF NEW YORK.

ARTIFICIAL LIMB.

15,006. Specification of Reissued Letters Patent. Reissued Dec. 14, 1920.

Original No. 1,213,114, dated January 16, 1917, Serial No. 94,813, filed May 1, 1916. Application for reissue filed August 20, 1919. Serial No. 318,815.

*To all whom it may concern:*

Be it known that I, LOUIS C. LAWRENCE, a citizen of the United States, residing at Brooklyn, in the county of Kings and State of New York, have invented certain new and useful Improvements in Artificial Limbs; and I do hereby declare the following to be a full, clear, and exact description of the invention, such as will enable others skilled in the art to which it appertains to make and use the same.

This invention relates to artificial limbs, and more particularly to that type wherein the parts forming the limb may be adjustably secured together to permit a limb of standard dimensions being adjustable within a wide range of sizes.

An object of this invention is to provide an improved means for forming sections of an artificial limb of a plurality of plates which are shaped to simulate the general configuration of a limb and these sections are adjustably secured to each other to permit an adjustment thereof.

A further object of this invention is the provision of an improved type of joint for leg sections in which the parts constituting said joint are adjustably secured to each other.

Figure 1:
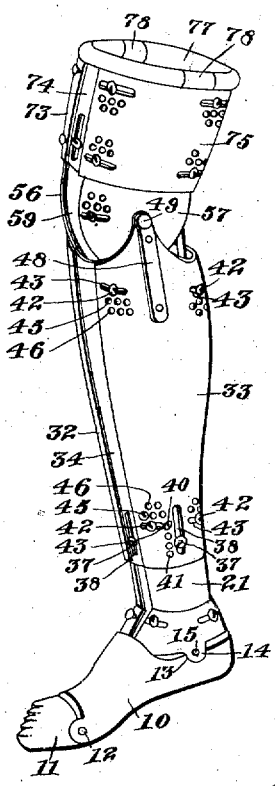
Figure 3:
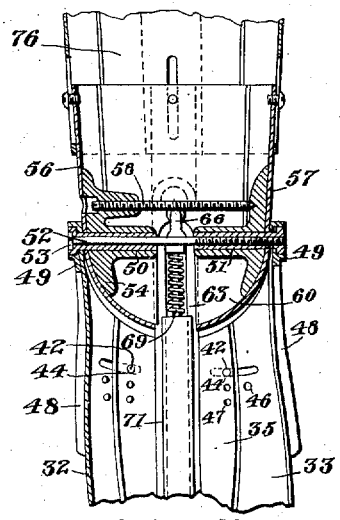
Figure 4:
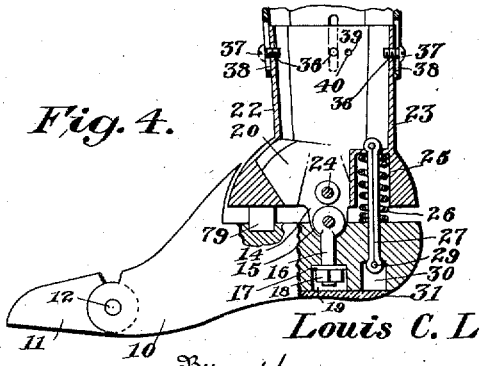
Figure 2:
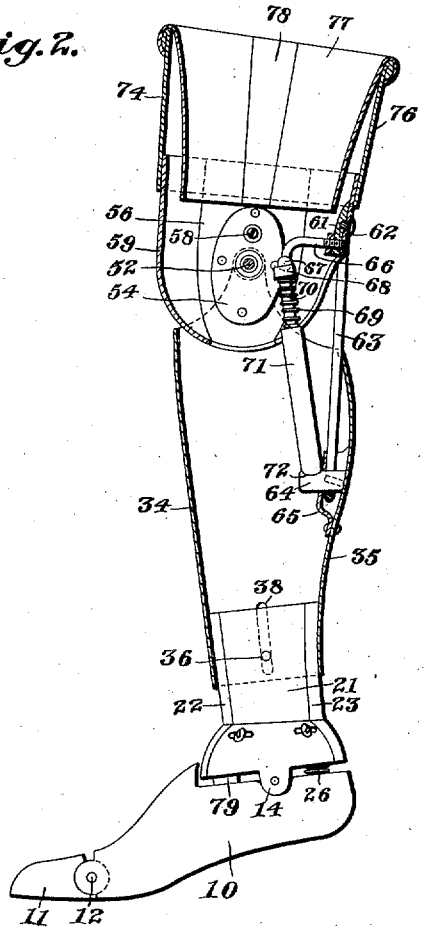
Figure 8:
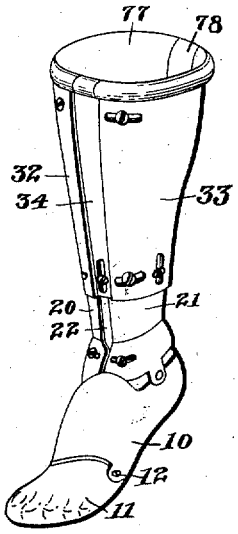
Figure 5:
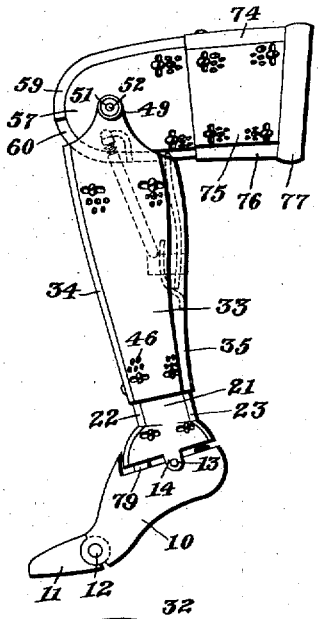
Figure 6:
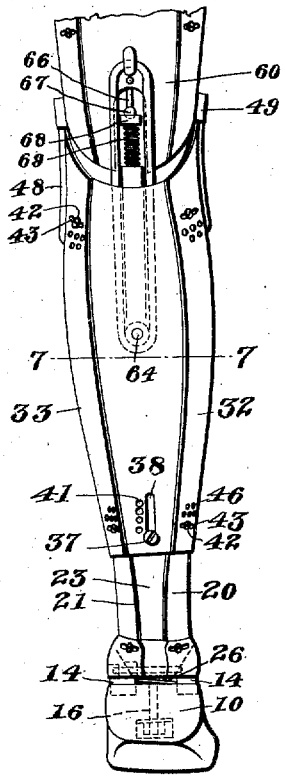
Figure 7:
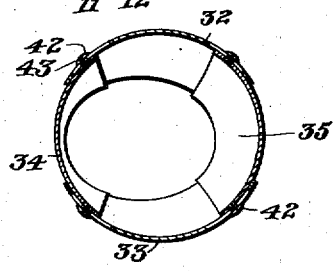

Further objects will be apparent from the following specification, appended claims, and drawings, in which:

Figure 1 is a perspective view of an artificial leg constructed in accordance with this invention, Fig. 2 is a vertical sectional view therethrough, Fig. 3 is a similar view across the knee, Fig. 4 is a sectional view through the ankle, Fig. 5 is a side elevation showing the knee bent, Fig. 6 is a rear elevation, Fig. 7 is a cross sectional view on line 7—7 of Fig. 6, and Fig. 8 is a perspective view of a modification.

This invention provides for a simple construction of an artificial limb wherein standard parts may be used to form limbs of different proportions, and certain of said parts being interchangeable in modified forms.

Referring to the drawings, 10 indicates a foot, having a toe section 11, hingedly secured thereto as at 12 and this foot section is recessed as at 13 to receive the knuckles 14 of an ankle section in which the pintle 15 is disposed. This pintle passes through the eye-bolt 16 which passes through the foot section to receive the washer 17 and nut 18 in the socket 19.

The ankle section is formed of the side plates 20 and 21, and the front and rear plates 22 and 23 respectively, and the side plates terminate at their lower edges in the knuckles 14. These side plates are enlarged at the knuckles and the pintle 15 passes through one of the knuckles freely, but has threaded engagement with the other, so that the side plates may be drawn together when desired, and to cause outward movement of said plates, a screw 24 is provided which has threaded engagement with one side plate and bears against the other side plate to extend the plates when rotated in one direction. The back plate of the ankle section has a socket 25 formed therein in which a compression spring 26 is placed to bear between the end of the socket and the foot section, and a tension cord 27 is placed inside of this spring. This cord has one end secured by the pin 28 bearing on the outer face of the socket, and by the pin 29 set in the socket 30 formed in the foot section. The sockets 19 and 30 are covered by the pad 31 secured to the heel of the foot section.

The ankle section is adjustably secured to a leg section comprising the side plates 32 and 33, and the front and rear plates 34 and 35 respectively by having the upper ends of the plates of the ankle sections provided with the slots 36, in which screws 37, which pass through the slots 38 in the leg sections pass. The screws 37 serve as temporary supports and to afford a permanent lock, the threaded holes 39 are formed in the ankle sections to receive screws 40 which may pass through any of the series of holes 41 formed in the leg sections. The side plates and front and back plates are curved and overlap each other, as shown more particularly in the enlarged cross-section, Fig. 7, so as to be circumferentially adjustable to form a socket of the desired diameter. After adjustment they may be secured together by the screws 42, which pass through the slots 43 and into the threaded holes 44, and by the permanent lock comprising the screws 45 which may pass through any of the holes 46 when they coincide with either of the holes 47. The general locking means is repeated where desired.

For an amputation in the calf below the knee, the artificial limb will terminate at this point, as shown in Fig. 8, and the four curved overlapping plates 32, 33, 34 and 45, circumferentially adjustable form a socket which is expansible and contractible to be self-adjusting to the stump, yet always closed at the sides and affording a complete and firm support for the stump. The socket may be provided with an internal pad 77, 78, as hereinafter described.

In the construction shown in Figs. 1 to 6 which illustrates an artificial limb for a thigh amputation, the side plates 32, 33 may have braces 48 secured thereto as by rivets or otherwise, and these braces terminate in the heads 49, which are formed to receive the heads of sleeves 50 and 51, of which, the sleeve 51 is internally threaded to receive the threaded portion of a pintle 52. The pintle 52 has a slotted head 53 formed thereon to receive a screw driver or other implement for adjusting the relative distance of the sleeves 50 and 51. The sleeves 50 and 51 are carried by fittings 54 and 55, which are carried by side plates 56 and 57 of a knee section, and these fittings also support a screw 58 which is carried in a threaded socket of the fitting 54 and adapted to bear against the inner face of the fitting 55. By the use of the screws 52 and 58, it is seen that the side plates 56 and 57 may be varied in position with respect to each other, as one of these screws contracts the general dimension of the knee, while the other extends it.

The side plates of the knee also carry the front and back plates 59 and 60 by the fastening means already described, and of these two plates, the rear plate has a fitting 61 secured therein, which is grooved on the outer face as at 62, to receive a tension cord 63, which passes into the leg section where it is attached to a block 64 in the leg section. This block is held to the back plate of the leg section, and it passes through a guard 65 which is also attached to the back plate as shown in Fig. 2.

The fitting 61 supports an arm 66 which terminates in a ball 67 to form a ball and socket joint with a socket formed in the end of a bar 68. A compression spring 69 is coiled about the stem 70 of the bar 68, and this spring passes into a guard 71 which may have its lower end rounded to bear in the cupped face 72 on the block 64. It is evident how the compression spring and tension cord act when the leg is worn as they permit the knee being bent and held partially in bent position and they cushion the action of the limb in being bent from one position to the other.

The knee section is adjustably secured to the thigh-receiving section as by screw and slot connections and permanent locking means as above described with reference to the connection of the ankle section to the leg section. This thigh-receiving section is composed of four overlapping curved plates 73, 74, 75 and 76 circumferentially adjustable by screws and slots in the same manner as above described with reference to the plates 32, 33, 34 and 35 of the leg section.

This thigh-receiving section is provided with an internal pad 77 which is secured to the outer faces of the upper edges thereof, and this pad passes downwardly in these thigh sections. This pad may be made of sections of which, the larger ones may be of sizes to properly form a pad in the smallest formation of the thigh, and these larger sections may be moved apart to receive the inserts 78 therebetween in the larger sizes of the thigh section. The inserts 78 will vary in the different sizes of the limb.

Fig. 8 shows the pad applied on the leg or calf section, and its application is similar to that described above.

The foot and ankle sections may have a buffer 79 placed therebetween as shown in Fig. 4 to cushion the action between the foot and ankle sections.

It is thought that the foregoing description clearly sets forth the adjustability and mode of application of this invention, and that further description is unnecessary.

Furthermore, no limitation is implied by the few forms shown, and modifications may be made within the scope of the appended claims.

Having thus described this invention, I claim:

1. An artificial limb of the class described comprising sections pivotally joined together, each of said sections comprising a plurality of shaped plates adjustably secured to each other for lateral adjustment with respect to each other and a joint for said sections comprising a plurality of shaped plates adjustably secured to each other, said sections comprising said joint having longitudinal adjustment with the plates of the adjacent section.

2. An artificial limb of the class described comprising an adjustable joint section, said joint section being formed of a plurality of overlapping shaped plates, said plates being adjustably secured to each other for lateral adjustment, a pintle carried by one of said plates, having threaded engagement with another of said plates to draw said plates together, and a threaded stem carried by one of the plates engaging the opposite plate to separate said plates and enlarge the general dimensions of said joint section.

3. An artificial limb of the class described comprising a foot, an ankle section and a leg section, said foot section having its upper face recessed to receive fastening means carried by the ankle section, said ankle and leg sections comprising complemental sections having their edges overlapping, and fastening means carried by said sections to hold said sections in any desired relation.

4. An artificial limb of the class described comprising a foot, an ankle section and leg section, said foot having its upper face recessed to receive fastening means, an eyebolt carried by said foot, said ankle section comprising four complemental sheet metal sections fitted to each other, side plates of said ankle section, bearings formed on the lower ends of said side plates, said leg section comprising four complemental sheet metal sections fitted to have their edges overlapping, said leg sections having their lower ends slotted to permit a vertical adjustment over said ankle sections, fastening means for the sections of said leg and ankle portions and said leg sections having transverse slots formed therein to receive fastening means carried by some of said sections for lateral adjustment of said plates comprising said leg section with respect to each other.

5. An artificial limb of the class described comprising a foot, an ankle section and a leg section, said foot having its upper face recessed to receive fastening means, an eyebolt carried by said foot, said ankle section comprising four fitted sheet metal sections having their edges overlapping, the front plate of said ankle section having an inwardly directed lug from a lower edge thereof, a cushion between said lug and said foot, the back plate of said ankle section having a socket formed in the lower end thereof, a spring in said socket bearing on said foot, a tension cord connecting said back plate to said foot, side plates connecting said front and back plates being adjustably connected thereto, bearings formed on the lower ends of said side plates to rest in the recessed portions of said foot and fastening means carried by the several sections to adjustably secure them to each other.

6. An artificial limb of the class described comprising a leg section of four fitted sheet metal sections having their edges overlapping, some of the plates comprising the leg section having transverse slots formed therein, fastening means carried by others of said plates passing through said transverse slots, said plates having their transverse slots therein also having a plurality of individual holes formed therein, detachable fastening means passing through some of said individual holes into the underlying portions of others of said plates, a back plate included in said leg section, a block secured to the inside of said back plate, a knee section comprising four overlapping shaped plates, a back in said knee section, said back plate being recessed to receive a tension cord, a tension cord in said recess having its lower end encircle the block secured to the back section of the leg, a bracket secured in said back plate, said bracket having a depending head, a locking means in bearing relation between said depending head and the block secured to the back of the leg section, said locking means comprising a recessed block to engage the depending head, a stem formed on said block, a compression spring coiled about said stem, a tube to receive said compression spring and said tube having a bearing at its lower end on the block secured to the back plate of the leg section.

7. An artificial limb having a stump-receiving section formed by a plurality of curved plates which overlap each other and are adjustable to form an expansible and contractible socket closed at the sides and means for maintaining said plates in adjustment.

8. An artificial limb having a stump receiving section formed of a plurality of curved plates which overlap each other and are adjustable to form an expansible and contractible socket closed at the sides and screw means to maintain said plates in adjustment.

In testimony whereof I affix my signature.

LOUIS C. LAWRENCE.